US006579469B1

(12) United States Patent
Nicholson et al.

(10) Patent No.: US 6,579,469 B1
(45) Date of Patent: *Jun. 17, 2003

(54) CYANOACRYLATE SOLUTIONS CONTAINING PRESERVATIVES

(75) Inventors: William S. C. Nicholson, Raleigh, NC (US); Upvan Narang, Raleigh, NC (US); Ubonwan A. Stewart, Durham, NC (US); Daniel L. Hedgpeth, Raleigh, NC (US); Ibraheem T. Badejo, Morrisville, NC (US); Lawrence H. Mainwaring, Raleigh, NC (US)

(73) Assignee: Closure Medical Corporation, Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/430,180

(22) Filed: Oct. 29, 1999

(51) Int. Cl.$^7$ ................................. C09K 3/00
(52) U.S. Cl. .................... 252/182.11; 252/182.18; 252/182.19; 422/1; 422/22; 522/152; 523/111; 523/118; 524/81; 524/259; 524/295; 524/296; 524/297; 524/310; 524/315; 524/317; 524/369; 524/470; 524/375; 524/486
(58) Field of Search .................... 252/182.11, 182.18, 252/182.29; 524/310, 295, 296, 297, 315, 317, 486, 470, 375, 369, 259, 81; 521/71, 74, 77, 173; 422/1, 22; 523/111, 118; 522/152

(56) References Cited

U.S. PATENT DOCUMENTS

| | | |
|---|---|---|
| 2,721,858 A | 10/1955 | Joyner et al. |
| 3,254,111 A | 5/1966 | Hawkins et al. |
| 3,886,125 A | 5/1975 | Chromecek |
| 3,928,556 A | 12/1975 | Sweger |
| 3,932,602 A | 1/1976 | Sweger |
| 3,940,362 A | 2/1976 | Overhults |
| 4,073,291 A | 2/1978 | Marvel et al. |
| 4,076,685 A | 2/1978 | Kogler |
| 4,127,382 A | 11/1978 | Perry |
| 4,200,549 A * | 4/1980 | Okamura |
| 4,303,066 A | 12/1981 | D'Andrea |
| 4,307,216 A | 12/1981 | Shiraishi et al. |
| 4,310,509 A | 1/1982 | Berglund et al. |
| 4,313,865 A | 2/1982 | Teramoto et al. |
| 4,321,180 A | 3/1982 | Kimura et al. |
| 4,322,398 A | 3/1982 | Reiner et al. |
| 4,323,557 A | 4/1982 | Rosso et al. |
| 4,446,124 A | 5/1984 | Fox, Jr. et al. |
| 4,486,488 A | 12/1984 | Pietsch et al. |
| 4,560,723 A | 12/1985 | Millet et al. |
| 4,579,731 A | 4/1986 | Fox, Jr. et al. |
| 4,603,152 A | 7/1986 | Laurin et al. |
| 4,626,428 A | 12/1986 | Weisberg et al. |
| 4,677,143 A | 6/1987 | Laurin et al. |
| 4,720,513 A | 1/1988 | Kameyama et al. |
| 4,797,282 A | 1/1989 | Wahlig et al. |
| 4,892,736 A | 1/1990 | Goodson |
| 4,910,259 A | 3/1990 | Kindt-Larsen et al. |
| 4,931,282 A | 6/1990 | Asmus et al. |
| 4,940,579 A | 7/1990 | Randen |
| 4,980,086 A | 12/1990 | Hiraiwa et al. |
| 5,019,096 A | 5/1991 | Fox, Jr. et al. |
| 5,045,601 A | 9/1991 | Capelli et al. |
| 5,061,286 A | 10/1991 | Lyle |
| 5,069,907 A | 12/1991 | Mixon et al. |
| 5,093,105 A | 3/1992 | Flanagan et al. |
| 5,143,071 A * | 9/1992 | Keusch et al. ............... 128/640 |
| 5,154,929 A | 10/1992 | Shibata et al. |
| 5,180,585 A | 1/1993 | Jacobson et al. |
| 5,219,325 A | 6/1993 | Hennink et al. |
| 5,254,132 A | 10/1993 | Barley et al. |
| 5,259,835 A | 11/1993 | Clark et al. |
| 5,306,482 A | 4/1994 | Tartaglia et al. |
| 5,324,520 A | 6/1994 | Dunn et al. |
| 5,326,567 A | 7/1994 | Capelli |
| 5,328,687 A | 7/1994 | Leung et al. |
| 5,354,790 A * | 10/1994 | Keusch et al. ............... 523/300 |
| 5,368,858 A | 11/1994 | Hunziker |
| 5,447,725 A | 9/1995 | Damani et al. |
| 5,480,935 A * | 1/1996 | Greff et al. .................. 524/776 |
| 5,494,481 A * | 2/1996 | Anderberg .................. 452/176 |
| 5,514,371 A | 5/1996 | Leung et al. |
| 5,514,372 A | 5/1996 | Leung et al. |
| 5,530,037 A * | 6/1996 | McDonnell et al. ........... 522/79 |
| 5,575,997 A | 11/1996 | Leung et al. |
| 5,582,834 A | 12/1996 | Leung et al. |
| 5,589,180 A | 12/1996 | Hind |
| 5,620,700 A | 4/1997 | Berggren et al. |
| 5,624,669 A | 4/1997 | Leung et al. |
| 5,665,817 A * | 9/1997 | Greff et al. .................. 524/776 |
| 5,684,042 A | 11/1997 | Greff et al. |
| 5,686,099 A | 11/1997 | Sablotsky et al. |
| 5,730,994 A | 3/1998 | Askill et al. |
| 5,753,699 A | 5/1998 | Greff et al. |

(List continued on next page.)

FOREIGN PATENT DOCUMENTS

| | | |
|---|---|---|
| EP | 0 865 787 | 9/1998 |
| WO | 95/09607 | 4/1995 |
| WO | 99/18950 | 4/1999 |
| WO | WO 99/23011 | 5/1999 |
| WO | WO 99/42142 | 8/1999 |

OTHER PUBLICATIONS

Lars Wetter et al., "Effects of Zinc Oxide in an Occlusive, Adhesive Dressing on Granulation Tissue Formation," *Acta Pharmacol Toxicol Suppl*, vol. 59(7), pp. 184–187 (1986).

(List continued on next page.)

Primary Examiner—Margaret Medley
(74) *Attorney, Agent, or Firm*—Oliff & Berridge, PLC

(57) ABSTRACT

An adhesive composition that contains a preservative is particularly useful as a medical adhesive and can include alkyl cyanoacrylate monomers. The preservative is preferably soluble in the monomer. The composition may optionally be sterilized by placing a mixture of a polymerizable adhesive monomer and a preservative in a container, sealing the container, and sterilizing the mixture and the container.

60 Claims, No Drawings

U.S. PATENT DOCUMENTS

| | | | |
|---|---|---|---|
| 5,760,102 A | * 6/1998 | Hall et al. | 523/120 |
| 5,762,919 A | 6/1998 | Greff et al. | |
| 5,783,177 A | 7/1998 | Greff et al. | |
| 5,807,563 A | 9/1998 | Askill et al. | |
| 5,811,091 A | 9/1998 | Greff et al. | |
| 5,866,106 A | 2/1999 | Papay | |
| 5,902,594 A | 5/1999 | Greff et al. | |
| 5,928,611 A | 7/1999 | Leung | |
| 5,998,472 A | * 12/1999 | Berger et al. | 514/527 |
| 6,086,906 A | 7/2000 | Greff et al. | |
| 6,090,397 A | 7/2000 | Lee et al. | |
| 6,102,205 A | 8/2000 | Greff et al. | |
| 6,143,805 A | * 11/2000 | Hickey et al. | 522/152 |
| RE36,994 E | * 12/2000 | Anderberg | 452/176 |
| 6,183,593 B1 | * 2/2001 | Narang et al. | 156/327 |
| 6,191,202 B1 | * 2/2001 | Greff et al. | 524/310 |
| 6,248,800 B1 | 6/2001 | Greff et al. | |
| 6,352,704 B1 | * 3/2002 | Nicholson et al. | 424/407 |

OTHER PUBLICATIONS

Lars Wetter et al., "Effects of Zinc Oxide in an Occlusive Adhesive Dressing on Granulation Tissue Formation," *Scand. J. Plast. Reconsr. Surgery*, vol. 20, pp. 165–172 (1986).

DERMAGRAN™ Product Literature, Derma Sciences (date unknown).

M. Fan et al., "Effect of Chlorhexidine Varnish System on Streptococcus Mutant in Fissure Plaques," *Zhonghua Kouqiang Yixue Zazhi*, Col. 32(5), pp. 269–271 (1997) (abstract).

* cited by examiner

CYANOACRYLATE SOLUTIONS CONTAINING PRESERVATIVES

BACKGROUND OF THE INVENTION

1. Field of the Invention

The invention relates to monomer and polymer adhesive and sealant compositions, and to their production for industrial and medical uses.

2. State of the Art

Monomer and polymer adhesives are used in both industrial (including household) and medical applications. Included among these adhesives are the 1,1-disubstituted ethylene monomers and polymers, such as the α-cyanoacrylates. Since the discovery of the adhesive properties of such monomers and polymers, they have found wide use due to the speed with which they cure, the strength of the resulting bond formed, and their relative ease of use. These characteristics have made α-cyanoacrylate adhesives the primary choice for numerous applications such as bonding plastics, rubbers, glass, metals, wood, and, more recently, biological tissues.

It is known that monomeric forms of α-cyanoacrylates are extremely reactive, polymerizing rapidly in the presence of even minute amounts of an initiator, including moisture present in the air or on moist surfaces such as animal tissue. Monomers of α-cyanoacrylates are anionically polymerizable or free radical polymerizable, or polymerizable by zwitterions or ion pairs to form polymers. Once polymerization has been initiated, the cure rate can be very rapid.

Medical applications of 1,1-disubstituted ethylene adhesive compositions include use as an alternate or an adjunct to surgical sutures and staples in wound closure as well as for covering and protecting surface wounds such as lacerations, abrasions, burns, stomatitis, sores, and other surface wounds. When an adhesive is applied, it is usually applied in its monomeric form, and the resultant polymerization gives rise to the desired adhesive bond.

For example, polymerizable 1,1-disubstituted ethylene monomers, and adhesive compositions comprising such monomers, are disclosed in U.S. Pat. No. 5,328,687 to Leung et al. Suitable methods for applying such compositions to substrates, and particularly in medical applications, are described in, for example, U.S. Pat. Nos. 5,582,834, 5,575,997, and 5,624,669, all to Leung et al.

It is known to use cyanoacrylate adhesives to deliver bioactive agents to a wound site. For example, the above patents to Leung et al. disclose such technology in some detail. Examples of such bioactive agents include antimicrobial agents to be released into the wound. U.S. Pat. Nos. 5,684,042; 5,753,699; 5,762,919; 5,783,177; 5,811,091; and 5,902,594, all to Greff et al., disclose that an antimicrobially effective amount of an antimicrobial agent may be incorporated into the polymerizable cyanoacrylate ester composition to promote wound healing and retard infection of the wound. See col. 2, lines 50–53 and Abstract of the '699 patent. In order to achieve an antimicrobial effect, an antimicrobial complex of iodine molecules with a biocompatible polymer is used. The iodine/polymer complexes are dispersible in the cyanoacrylate ester. See col. 7, lines 45–48 of the '699 patent. However, the iodine/polymer complexes were not soluble in the cyanoacrylate ester. See Table I, col. 12, line 55–col. 13, line 14 of the '699 patent. See also, U.S. Pat. Nos. 5,730,994 and 5,807,563 to Askill et al. and WO 99/18950 to Berger et al.

It is also important to prevent the introduction of microorganisms to the wound site during treatment of the wound. Cyanoacrylate compositions, at least those for use in medical applications, are generally initially sterile. That is, the compositions as manufactured do not contain live microorganisms. However, through improper handling of the compositions or repeated exposure of the compositions to a non-sterile environment, such as with multiple use applicators, microorganisms that are present in the air may be introduced into a cyanoacrylate composition and survive, resulting in the contamination of the composition. Although the source for this characteristic is not understood, it has been observed that cyanoacrylate compositions inherently possess some antimicrobial activity. In particular, cyanoacrylate compositions themselves prevent the growth of some types of microorganisms within the composition. However, cyanoacrylate compositions by themselves do not possess such a broad spectrum of antimicrobial activity that all amounts of every type of microorganisms would not grow in the compositions.

A way to inactivate microorganisms in the cyanoacrylate compositions is to sterilize the composition. However, sterilization of α-cyanoacrylate adhesive compositions is often difficult to achieve. For example, widely practiced methods of sterilization, such as dry and moist heat sterilization, ionizing radiation, exposure to gas, and aseptic filtration, are not always convenient for use with monomeric cyanoacrylate compositions. Problems sometimes arise due to polymerization of the monomer during the sterilization process. In many cases, sterilization-induced polymerization is so severe that the resulting product is unusable.

Additionally, even if complete sterilization of cyanoacrylate compositions is achieved, such that all microorganisms present in the composition are destroyed, improper handling or exposure to air after sterilization could result in introduction and growth of microorganisms in the cyanoacrylate compositions.

Thus, a need exists for improved monomer cyanoacrylate adhesive compositions, especially for medical uses, wherein the growth of microorganisms in a cyanoacrylate composition is prevented and the performance of the adhesive composition is not compromised.

SUMMARY OF THE INVENTION

The present invention provides a monomeric adhesive composition comprising an antimicrobial preservative agent and a polymerizable alkyl cyanoacrylate monomer. In embodiments, the antimicrobial agent is soluble in the monomer at room temperature and the resultant composition is stable for at least a given amount of time. However, in some specific embodiments, complete solubility may not be required. Production of the composition includes mixing a polymerizable alkyl cyanoacrylate monomer and an antimicrobial agent in a container. The monomeric adhesive composition may be sterilized. Production of the sterilized composition includes placing a polymerizable alkyl cyanoacrylate monomer and an antimicrobial agent in a container, sealing the container and sterilizing the container and the mixture. Optionally, the container used to hold the composition in embodiments of the present invention can be a multi-use container or packaging system. The compositions produced, packaged and sterilized according to the present invention are stable, and have extended utility, as compared to adhesive compositions of the prior art.

DETAILED DESCRIPTION OF PREFERRED EMBODIMENTS

According to the present invention, a monomeric adhesive composition comprises a preservative agent and a polymerizable alkyl cyanoacrylate monomer.

An antimicrobial preservative agent is a compound that either destroys or usefully suppresses the growth or metabolism of a variety of microscopic or submicroscopic life forms. Such life forms include, but are not limited to microorganisms, bacteria, fungi, algae, protozoa, and viruses. The agent preferably has a positive antimicrobial effect against at least microorganisms. In particular, the agent should be effective so that most, and preferably all, of the microscopic or submicroscopic life forms are killed, without compromising the monomeric adhesive composition. Preferably, the agent is effective at reducing or maintaining the level of microbes in the composition at a commercially acceptable level, or at a level as regulated by an appropriate governing body, such as the USP (United States Pharmacopia) or the European Pharmacopia, or recommended by associations such as the Cosmetic, Toiletry and Fragrance Association.

Preferably, in embodiments of the present invention, the preservative is effective at killing, or at least preventing the growth of, any microbes that may be initially present in the adhesive formulation, or that may be subsequently introduced into the adhesive formulation during normal use. In embodiments where the adhesive formulation containing the preservative is sterilized, the preservative is particularly useful in killing or preventing the growth of any microbes that may be subsequently introduced into the adhesive formulation during normal use thereof, such as during normal use of a multiple-use applicator system, where air and contaminants may be introduced into the applicator. The present invention, in embodiments, is applicable to single-use containers or applicators, where it is desired to maintain a high degree of prolonged sterility and stability of the composition, by supplementing an optional sterilization treatment by addition of the antimicrobial agent. Likewise, in embodiments, the present invention is also particularly applicable to multiple-use containers or applicators, where it is desired to maintain a high degree of prolonged sterility and stability of the composition against microbial action despite loss of initial sterility upon first use of the composition.

The preservative of the present invention operates to destroy microorganisms that may be present or grow in the polymerizable alkyl cyanoacrylate monomer composition. Although some preservatives may also advantageously function as polymerization inhibitors, in embodiments of the present invention the preservative does not operate as such, and does not affect polymerization of the monomer material.

The preservative may be selected from among known anti-microbial agents. In embodiments, the preservative may be selected from among known preservatives, including, but not limited to, parabens and cresols. For example, suitable parabens include, but are not limited to, alkyl parabens and salts thereof, such as methylparaben, methylparaben sodium, ethylparaben, propylparaben, propylparaben sodium, butylparaben, and the like. Suitable cresols include, but are not limited to, cresol, chlorocresol, and the like. The preservative can also be selected from other known agents including, but not limited to, hydroquinone, pyrocatechol, resorcinol, 4-n-hexyl resorcinol, 3a,4,7,7a-tetrahydro-2-((trichloromethyl)thio)-1H-isoindole-1,3(2H)-dione, benzalkonium chloride, benzalkonium chloride solution, benzethonium chloride, benzoic acid, benzyl alcohol, cetylpyridinium chloride, chlorobutanol, dehydro acetic acid, o-phenylphenol, phenol, phenyl ethyl alcohol, potassium benzoate, potassium sorbate, sodium benzoate, sodium dehydroacetate, sodium propionate, sorbic acid, thimerosal, thymol, phenylmercuric compounds such as phenylmercuric borate, phenylmercuric nitrate and phenylmercuric acetate, formaldehyde, and formaldehyde generators such as the preservatives Germall II® and Germall 115® (imidazolidinyl urea, available from Sutton Laboratories, Charthan, N.J.). In embodiments, mixtures of two or more preservatives can also be used.

Furthermore, various other compounds can be screened for their antimicrobial and preservative effects, and then selected based on the results of this screening. For example, compounds can be tested for their antimicrobial and preservative effectiveness by one or more of a USP preservative test regimen, a USP microbial limits test, a USP bacteriostasis and fungistasis test, and a USP antibiotics-microbial assay. See, for example, USP 23<51>, Supplement 8, "Antimicrobial Effectiveness Testing," the entire disclosure of which is incorporated herein by reference.

According to the present invention, a selection process may be used to select appropriate agents for use in specific polymerizable alkyl cyanoacrylate monomer compositions in accordance with the invention. Such a screening process can be used to select from among the various known preservative, or from those agents determined by the above USP testing regimens. The preservative should be soluble in the monomer composition and without significantly adversely affecting the stability of the monomer composition. In addition, in embodiments, the preservative in combination with the monomer composition should also be compatible with one or more sterilization procedures. Thus, a suitable procedure for selecting an agent generally involves selecting a group of potential agents, assessing their solubility and stability in the monomer composition, and testing for their compatibility with one or more sterilization procedures.

Potential agents for testing can readily be selected by one of ordinary skill in the art from known sources. For example, such sources can include the USP list of approved agents, or other such lists maintained by various governmental or non-governmental agencies, such as the U.S. Food and Drug Administration (US FDA).

Once a potential agent is selected, it can be tested for solubility and stability in the monomer composition, such as by mixing an appropriate amount of the agent with a desired amount of the monomer composition and any other desired additives. It is preferred that the agent is soluble, i.e., dissolves, in the monomer composition.

Solubility is preferred because a higher antimicrobial effect can be provided by the agent when it is dispersed throughout the monomer composition in the form of a solution. If the agent is not in the form of a solution, then it is possible that the agent may settle or otherwise agglomerate, and thereby not provide an antimicrobial effect to all of the monomer composition.

Thus, it is preferred in embodiments that the agent exhibits a uniform concentration, or substantially so, throughout the monomer composition. Of course, where excess agent is added to the composition, i.e., in an amount above the solubility point of the agent, it is acceptable that a portion of the agent remains undissolved in the composition so long as it does not significantly interfere with the stability and/or use of the composition. Furthermore, the antimicrobial agent can be provided by a component that is not itself necessarily soluble in the monomer composition. For example, various non-polymer stabilized agents, such as some elemental metals and metal compounds, which themselves are not soluble in the monomer composition, can provide an antimicrobial agent, such as metal ions, which is soluble in the monomer composition.

A second screening procedure is to test the potential agent for stability with the monomer composition. This screening procedure can also be performed by mixing an appropriate amount of the agent with a desired amount of the monomer composition and any other desired additives. Stability is preferred because it is important to maintain the stability of the monomer composition within acceptable levels, such as commercially acceptable levels whereby the composition is not prematurely polymerized prior to application of the monomer composition to a desired substrate. One possible measure of the stability of the composition, other than a visual examination of the properties of the composition, is a measure of any changes in viscosity of the composition from a time prior to adding the agent to a time after adding the agent. For example, dramatic increases or decreases in the viscosity can indicate instability of the composition, such as premature polymerization or other chemical degradation of the monomer composition or components thereof.

In embodiments of the present invention, it is preferred that the agent exhibit stability in the monomer composition for at least five minutes after mixing or dissolving the agent in the polymerizable monomer compound. More preferably, stability of the monomer composition is maintained for at least one hour, preferably ten hours, and more preferably twenty-four hours after mixing the agent with the polymerizable monomer compound. Even more preferably, stability of the monomer composition is maintained for a time period sufficient to provide a commercially significant shelf-life to the monomer composition, or even an extended shelf-life as compared to similar monomer compositions not including such an agent. As used herein, "stability" refers to the resultant composition maintaining a commercially acceptable form for the prescribed amount of time. That is, the composition does not prematurely polymerize or otherwise change form or degrade to the point that the composition is not useful for its intended purpose. Thus, while some polymerization or thickening of the composition may occur, such as can be measured by changes in viscosity of the composition, such change is not so extensive as to destroy or significantly impair the usefulness of the composition.

Optionally, in embodiments of the present invention, the potential agent can be tested for its compatibility with one or more sterilization procedures. This optional screening procedure can also be performed by mixing an appropriate amount of the agent with a desired amount of the monomer composition and any other desired additives, and then subjecting the resultant composition to one or more sterilization procedures. Compatibility of the agent with one or more sterilization procedures is preferred in embodiments of the present invention because many uses of the polymerizable monomer compositions, such as many medical applications, require or prefer sterilized products. Following sterilization, the agent can exert antimicrobial action in killing or preventing growth of microbes that may be introduced into the pre-sterilized monomer compositions.

Of course, as will be apparent to those skilled in the art, the above selection procedures need not be conducted in any particular order, and need not be conducted sequentially. That is, the procedures can be conducted in any order, and can be conducted simultaneously, if desired. Likewise, not all of the procedures may be necessary, and other screening procedures may be used as necessary depending on particular applications.

The amount of preservative that is added to the monomer composition depends upon several factors, including, but not limited to, the specific preservative being used, the amount of the preservative suitable for use in the compositions, and whether and to what extent the preservative is regulated by the U.S. FDA (or other appropriate regulatory agencies or bodies of the United States or foreign countries). Benzoic acid may be present in a concentration of from about 0.05–0.1% of the adhesive composition. Benzyl alcohol may be present in a concentration of from about 0.5–5.0% of the adhesive composition. Butylparaben, ethylparaben, methylparaben, methylparaben sodium, propylparaben, and propylparaben sodium may each be present in a concentration of from about 0.001–0.2% of the adhesive composition. Suitable amounts of other preservatives can be determined by one of ordinary skill in the art, for example with reference to readily available resources such as S. Seymour Block, *Disinfection, Sterilization and Preservation*, 3$^{rd}$ Ed., Philadelphia:Lea & Febiger, 1983, the entirety of which is incorporated herein by reference.

Additionally, many compounds that are not polymer-stabilized, i.e., that are not complexed with or otherwise part of a polymer species, have antimicrobial properties. Such compounds can be either soluble or insoluble in the monomeric composition. Where the compounds are insoluble in the monomeric composition, they must be capable of releasing species, such as ions, which are soluble in the monomer composition and provide the antimicrobial effect. Thus such compounds either themselves are, or provide, the antimicrobial agent.

For example, many metals and metal compounds have antimicrobial properties. The antimicrobial agent may be selected from among known metal compounds or elemental metals, including, but not limited to, mercurial compounds, such as phenolmercuric chloride, phenolmercuric acetate, acetomeroctol, nitromersol, thimerosal, mercurochrome, mercuric chloride, and mercuric iodide; elemental metals, such as silver and copper; and metal compounds, such as copper chloride, copper sulfate, copper peptides, zinc chloride, zinc sulfate, silver nitrate, silver iodide, silver acetate, silver benzoate, silver carbonate, silver chloride, silver citrate, silver oxide, silver sulfate, and tincture of iodine. Copper peptides are discussed, for example, in "Copper: An Essential Element for Life," ProCyte Corporation, available at http://www.humatech.com/technology.html (Oct. 28, 1999), the entire disclosure of which is incorporated herein by reference. Further information on antimicrobial activities of metals can be found, for example, in S. Seymour Block, *Disinfection Sterilization and Preservation*, 3$^{rd}$ Ed., Philadelphia:Lea & Febiger, 1983, the entire disclosure of which is incorporated herein by reference. The ions from the metal, which constitute the antimicrobial agent, diffuse into and through the adhesive composition.

Various non-polymer stabilized compounds, such as the elemental metals and metal compounds, may be placed into the adhesive composition in any shape or configuration, as necessary or desired to provide the desired antimicrobial effect and the desired solubility of the antimicrobial agent in the monomer composition. In embodiments, for example, elemental copper and/or silver may be placed in the adhesive composition as spheres or balls, either hollow or solid, cubes or flat sheets or other shapes as desired. In such cases, the material should preferably dissolve to provide the desired concentration of antimicrobial agent in the monomer composition, or should release the antimicrobial agent at a desired level or rate to provide the antimicrobial effect. Although an excess of the agent may be present, such as to allow for adsorption and absorption by containers and changes in solubility levels due to, for example, changes in temperature, consumption of the agent, use of the monomer composition and the like, the excess should not significantly interfere with the use of the monomer composition.

Still further, various zinc compounds can be used in embodiments of the present invention. Such zinc compounds are preferred in embodiments because they possess multiple benefits, including the benefits of providing an antimicrobial effect while also helping to promote wound healing. The zinc compound can be present in the cyanoacrylate composition in various forms, such as zinc salts. For example, suitable zinc compounds include, but are not limited to, zinc salts of cyanoacrylic acid, zinc salts of cyanoacetic acid, zinc salts of dicyanoglutaric acid, zinc salts of rosin, zinc oxide, zinc salts of polycyanoacrylic acid, zinc salts of polyacrylic acid, zinc bacitracin, zinc salicylate, zinc stearate, zinc citrate, zinc lactate, mixtures thereof, and the like. Preferably, the zinc complexes and salts are of $Zn^{2+}$. The zinc complexes and/or salts can be incorporated into the cyanoacrylate composition, either prior to or concurrent with application and/or initiation; however, incorporation into the composition is preferred so that the antimicrobial effects can be utilized. Furthermore, once applied, the zinc compounds are particularly effective in promoting wound healing of leg ulcers, thermal burns, and the like. The amount of metal that is added to the monomer composition depends upon such factors as the form and combination of the metal used. The amount of metal can be determined by one of ordinary skill in the art using known techniques without undue experimentation.

Preferably, the agent is soluble in a monomer composition at room temperature (i.e., 20–25° C.) so that it may be added to the monomer composition without excessive heating of the monomer composition, and so that it remains soluble in the monomer composition during storage of the composition prior to use. The agent is selected such that it is compatible with the monomer (i.e., does not adversely affect polymerization, bond strength, cure properties, or shelf-life).

In embodiments, the adhesive composition has a viscosity of about 1–5000 centipoise, such as 3–600 centipoise, or 5–40 centipoise. The viscosity can be selected according to the proposed use—e.g., 4–50 centipoises for certain uses and 100–250 centipoises for other uses. Additionally, the composition may be a gel, e.g., 50,000–500,000 centipoise. A gel is a combination of a disperse phase with a continuous phase to produce a semisolid material. The viscosity of the adhesive composition may be measured with a Brookfield Viscometer at 25° C. Additionally, in embodiments where a sterilization treatment is applied, the viscosity of the composition should preferably be maintained or increased by a controlled and acceptable amount after sterilization.

Typically, for medical purposes, an adhesive should have a shelf-life of at least one year; however, an increased shelf-life beyond this provides increased economic advantages to both the manufacturer and the consumer. As used herein, shelf-life refers to the amount of time the container and composition therein can be held at approximately room temperature (21–25° C.) without degradation of the composition and/or container occurring to the extent that the composition and container cannot be used in the manner and for the purpose for which they were intended. Thus, while some degradation to either or both of the composition and container can occur, it must not be to such an extent that the composition and/or container is no longer useable. Appropriate amounts of preservative agents should be present so as to allow its effectiveness to be maintained throughout the shelf-life of the product. As used herein, an "extended shelf-life" refers to a shelf-life of at least 12 months, preferably at least 18 months, more preferably at least 24 months, and even more preferably, at least 30 months.

The present invention provides alkyl cyanoacrylate monomer compositions, that provide an extended shelf-life for industrial and/or medical uses, by killing or preventing growth of microbial entities such as microorganisms in the composition, in single-use and/or in multiple-use containers or applicators.

According to embodiments of the present invention, the stability, and thus the shelf-life, of some monomeric adhesive compositions can be further enhanced and extended through careful regulation of the packaging (i.e., dispensing into a container) and sterilizing procedures. In preferred embodiments, there is substantially no initiation of polymerization of the monomeric liquid adhesive compositions that affects the utility of the monomer or monomers caused by the sterilization process. In particular, a polymerizable alkyl cyanoacrylate monomer and a preservative are dispensed into a container without any, or without any substantial, initiation of polymerization. The container may then be sealed and, in embodiments, subjected to known sterilization techniques.

The monomeric composition may be packaged in any type of suitable container fabricated from materials including, but not limited to, glass, plastic, metal packages, and film-formed packages. Suitable containers include those into which the compositions can be dispensed and sterilized without unacceptable damage to, or degradation of, the container or the components of the monomer composition. Glass is especially preferred when sterilization is achieved with dry heat because of the lack of stability of many plastics at the temperatures used for dry heat sterilization (typically at least 160° C.). Examples of types of containers include, but are not limited to, ampoules, vials, syringes, pipettes, and the like.

In embodiments of the present invention, any suitable applicator can be used to apply the adhesive composition to a substrate. For example, the applicator can include an applicator body, which is formed generally in the shape of a tube having a closed end, an open end, and a hollow interior lumen, which holds a crushable or frangible ampoule. In this embodiment, the ampoule may contain the polymerizable monomer composition that is to be dispensed from the applicator. The ampoule may, in embodiments, be made of glass, plastic, ceramic, or the like, or any other brittle materials, and may be in any shape including, but not limited to, the shape of a tube, an oval, round, and the like.

In embodiments of the invention, the applicator can comprise elements other than an applicator body and an ampoule. For example, an applicator tip cam be provided on the open end of the applicator. The applicator tip can have a variety of suitable shapes, including, but not limited to, conical, cylindrical, chisel or polygonal shapes. The length and size of the tip can be varied depending on various application parameters. The tip may be detachable from the applicator body, or may be an integral part of the applicator. The tip further may be in the form of a nozzle for atomizing liquid solutions. The tip can be composed of any of a variety of materials including polymerized materials such as plastics, foams, rubber, thermosets, films, or membranes. Additionally, the applicator tip may be composed of materials such as metal, glass, paper, ceramics, cardboard, and the like. The applicator tip material may be porous, absorbent, or adsorbent in nature to enhance and facilitate application of the composition within the ampoule. In general, the only limitation on the materials used to fabricate the tip is that the tip must be sufficiently compatible with the composition to be dispensed that undesirable effects on the composition do not prevail during contact of the composition with the tip. Suitable designs for applicator tips that may be used according to the present invention are disclosed in, for example, U.S. Pat. No. 5,928,611 and U.S. patent applications Ser. No. 09/069,979, filed Apr. 30, 1998, and Ser. No. 09/069,875, filed Apr. 30, 1998, the entire disclosures of which are incorporated herein by reference.

The applicator and its related packaging can be designed as a single-use applicator or as a multi-use applicator. The present invention is particularly useful in multi-use applicators, because the preservative can inhibit the growth of microorganisms that may be introduced into the composition during use of the applicator. Suitable multi-use applicators are disclosed, for example, in U.S. patent application Ser. No. 09/385,030, filed Aug. 30, 1999, the entire disclosure of which is incorporated herein by reference.

Further, the applicator can comprise a screen or filter located within the applicator between the crushable ampoule and the open end of the applicator body. Such a screen or filter can be provided to stop any shards that are released upon breaking of the ampoule from exiting the applicator along with the composition being applied.

In embodiments, monomer compositions according to the invention are sterilized. The sterilization can be accomplished by techniques known to the skilled artisan, and is preferably accomplished by methods including, but not limited to, chemical, physical, and irradiation methods. Examples of physical methods include, but are not limited to, sterile fill, filtration, sterilization by heat (dry or moist) and retort canning. Examples of irradiation methods include, but are not limited to, gamma irradiation, electron beam irradiation, and microwave irradiation. Preferred methods are dry and moist heat sterilization and electron beam irradiation. In embodiments where a composition is to be used for medical applications, the sterilized composition should show low levels of toxicity to living tissue during its useable life.

In embodiments when the adhesive monomeric composition is sterilized, the sterilization should not destroy or counter the antimicrobial effect of the preservative. That is, in embodiments where a composition is to be sterilized, the type of sterilization used should preferably be selected based on the preservative used. For example, the parabens and cresols, which are soluble and stable in the monomer, are compatible with electron beam and dry heat sterilization methods. However, not all preservatives are compatible with such sterilization methods, and one method may be preferred over other methods. Thus, for example, where one or more sterilization procedures is to be used to sterilize the monomer composition, it is preferred that the above-described sterilization compatibility screening procedure be used.

However, a particular advantage of the present invention is that, in embodiments, sterilization processing of the composition and packaging can be eliminated. That is, where the preservative provides suitable and desired antimicrobial activity, subsequent sterilization of the adhesive composition can be dispensed with. The preservative thus provides benefits in terms of cost savings, by eliminating a subsequent sterilization step, and increased shelf-life, since some sterilization procedures tend to reduce shelf-life. Furthermore, in terms of multi-use packaging or containers, sterility is not lost after the first use because the preservative continues to provide antimicrobial action.

The monomer (including prepolymeric) composition may include one or more polymerizable monomers. In embodiments, at least one of the one or more monomers is an alkyl cyanoacrylate monomer, e.g., alkyl 2-cyanoacrylate. Preferred monomer compositions of the present invention, and polymers formed therefrom, are useful as tissue adhesives, sealants for preventing bleeding or for covering open wounds, and in other biomedical applications. They find uses in, for example, apposing surgically incised or traumatically lacerated tissues; retarding blood flow from wounds; drug delivery; dressing burns; dressing skin or other superficial or surface wounds (such as abrasions, chaffed or raw skin, and/or stomatitis); and aiding repair and regrowth of living tissue. Other preferred monomer compositions of the present invention, and polymers formed therefrom, are useful in industrial and home applications, for example in bonding rubbers, plastics, wood, composites, fabrics, and other natural and synthetic materials.

Monomers that may be used in this invention are readily polymerizable, e.g. anionically polymerizable or free radical polymerizable, or polymerizable by zwitterions or ion pairs to form polymers. Such monomers include those that form polymers, that may, but do not need to, biodegrade. Such monomers are disclosed in, for example, U.S. Pat. No. 5,328,687 to Leung, et al., which is hereby incorporated in its entirety by reference herein.

Preferred monomers for use in this invention are alkyl α-cyanoacrylates. These monomers are known in the art and have the formula

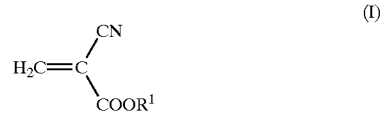

(I)

wherein $R^1$ is an alkyl or substituted alkyl group.

Examples of suitable alkyl and substituted alkyl groups include straight chain or branched chain alkyl groups having 1–16 carbon atoms; and straight chain or branched chain $C_1$–$C_{16}$ alkyl groups substituted with a haloalkyl group, a halogen atom, a cyano group, or a haloalkyl group.

In the cyanoacrylate monomer of formula (I), $R^1$ is preferably an alkyl group having 1–10 carbon atoms.

The α-cyanoacrylates of formula (I) can be prepared according to methods known in the art. U.S. Pat. Nos. 2,721,858 and 3,254,111, each of which is hereby incorporated in its entirety by reference, disclose methods for preparing α-cyanoacrylates. For example, the α-cyanoacrylates can be prepared by reacting an alkyl cyanoacetate with formaldehyde in a non-aqueous organic solvent and in the presence of a basic catalyst, followed by pyrolysis of the anhydrous intermediate polymer in the presence of a polymerization inhibitor. The α-cyanoacrylate monomers prepared with low moisture content and essentially free of impurities are preferred for biomedical use.

Preferred α-cyanoacrylate monomers used in this invention are alkyl α-cyanoacrylates including octyl cyanoacrylate, such as 2-octyl cyanoacrylate; dodecyl cyanoacrylate; 2-ethylhexyl cyanoacrylate; butyl cyanoacrylate such as n-butyl cyanoacrylate; ethyl cyanoacrylate; and methyl cyanoacrylate. More preferred monomers are n-butyl and 2-octyl α-cyanoacrylate. Monomers utilized for medical purposes in the present application should be very pure and contain few impurities (e.g., surgical grade). Monomers utilized for industrial purposes need not be as pure.

The composition may optionally also include at least one plasticizing agent that imparts flexibility to the polymer formed from the monomer. The plasticizing agent preferably contains little or no moisture and should not significantly affect the stability or polymerization of the monomer. Such plasticizers are useful in polymerized compositions to be used for closure or covering of wounds, incisions, abrasions, sores or other applications where flexibility of the adhesive is desirable. Some thickeners, such as poly-2-ethylhexylcyanoacrylate, can also impart flexibility to the polymer.

Examples of suitable plasticizers include acetyl tributyl citrate, dimethyl sebacate, triethyl phosphate, tri(2-ethylhexyl)phosphate, tri(p-cresyl)phosphate, glyceryl triacetate, glyceryl tributyrate, diethyl sebacate, dioctyl adipate, isopropyl myristate, butyl stearate, lauric acid, trioctyl trimellitate, dioctyl glutarate, and mixtures thereof. Preferred plasticizers are tributyl citrate and acetyl tributyl citrate. In embodiments, suitable plasticizers include polymeric plasticizers, such as polyethylene glycol (PEG) esters and capped PEG esters or ethers, polyester glutarates and polyester adipates.

The addition of plasticizing agents in amounts ranging from about 0.5 wt. % to about 25 wt. %, or from about 1 wt. % to about 20 wt. %, or from about 3 wt. % to about 15 wt. % or from about 5 wt. % to about 7 wt. % provides increased elongation and toughness of the polymerized monomer over polymerized monomers not having plasticizing agents.

The composition may also optionally include at least one thixotropic agent. Suitable thixotropic agents are known to the skilled artisan and include, but are not limited to, silica gels such as those treated with a silyl isocyanate. Examples of suitable thixotropic agents are disclosed in, for example, U.S. Pat. No. 4,720,513, the disclosure of which is hereby incorporated in its entirety.

The composition may also optionally include at least one natural or synthetic rubber to impart impact resistance, which is preferable especially for industrial compositions of the present invention. Suitable rubbers are known to the skilled artisan. Such rubbers include, but are not limited to, dienes, styrenes, acrylonitriles, and mixtures thereof. Examples of suitable rubbers are disclosed in, for example, U.S. Pat. Nos. 4,313,865 and 4,560,723, the disclosures of which are hereby incorporated in their entireties.

The composition may also optionally include both at least one anionic vapor phase stabilizer and at least one anionic liquid phase stabilizer. These stabilizing agents inhibit premature polymerization. Such stabilizing agents may also include mixtures of anionic stabilizing agents and radical stabilizing agents. Any mixture of stabilizers is included as long as the mixture does not inhibit the desired polymerization of the monomer.

The anionic vapor phase stabilizers may be selected from among known stabilizers, including, but not limited to, sulfur dioxide, boron trifluoride, and hydrogen fluoride. The amount of anionic vapor phase stabilizer that is added to the monomer composition depends on the identity of the liquid phase stabilizer(s) chosen in combination with it, the monomer to be stabilized, as well as the packaging material to be used for the composition. Preferably, each anionic vapor phase stabilizer is added to give a concentration of less than 200 parts per million (ppm). In preferred embodiments, each anionic vapor phase stabilizer is present from about 1 to 200 ppm, more preferably from about 10 to 75 ppm, even more preferably from about 10 to 50 ppm, and most preferably from 10 to 20 ppm. The amount to be used can be determined by one of ordinary skill in the art using known techniques without undue experimentation.

In embodiments, the vapor phase comprises, among other things, an anionic stabilizer that is sulfur dioxide. In embodiments, the vapor phase comprises, among other things, a stabilizer that is boron trifluoride or hydrogen fluoride. A combination of sulfur dioxide and boron trifluoride or hydrogen fluoride is preferable in some embodiments.

In embodiments, the liquid phase anionic stabilizer is a very strong acid. As used herein, a very strong acid is an acid that has an aqueous $pK_a$ of less than 1.0. Suitable very strong acidic stabilizing agents include, but are not limited to, very strong mineral and/or oxygenated acids. Examples of such very strong acids include, but are not limited to, sulfuric acid ($pK_a$-3.0), perchloric acid ($pK_a$-5), hydrochloric acid ($pK_a$-7.0), hydrobromic acid ($pK_a$-9), fluorosulfonic acid ($pK_a$<-10), chlorosulfonic acid ($pK_a$-10). In embodiments, the very strong acid liquid phase anionic stabilizer is added to give a final concentration of 1 to 200 ppm. Preferably, the very strong acid liquid phase anionic stabilizer is present in a concentration of from about 5 to 80 ppm, more preferably 10 to 40 ppm. The amount of very strong acid liquid phase anionic stabilizer to be used can be determined by one of ordinary skill in the art without undue experimentation.

Preferably, the very strong acid liquid phase anionic stabilizer is sulfuric acid, perchloric acid, or chlorosulfonic acid. More preferably, the very strong acid liquid phase anionic stabilizer is sulfuric acid.

In embodiments, sulfur dioxide is used as a vapor phase anionic stabilizer and sulfuric acid is used as a liquid phase anionic stabilizer.

The composition may also optionally include at least one other anionic stabilizing agent that inhibits polymerization. These agents are herein referred to as secondary anionic active agents to contrast them with the strong or very strong liquid phase anionic stabilizers, which are referred to hereinbelow as "primary" anionic stabilizers. The secondary anionic active agents can be included in the compositions to adjust the cure speed of the adhesive composition, for example.

The secondary anionic active agent would normally be an acid with a higher $pK_a$ than the primary anionic stabilizing agent and may be provided to more precisely control the cure speed and stability of the adhesive, as well as the molecular weight of the cured adhesive. Any mixture of primary anionic stabilizers and secondary active agents is included as long as the chemistry of the composition is not compromised and the mixture does not significantly inhibit the desired polymerization of the composition. Furthermore, the mixture should not, in medical adhesive compositions, show unacceptable levels of toxicity.

Suitable secondary anionic active agents include those having aqueous $pK_a$ ionization constants ranging from 2 to 8, preferably from 2 to 6, and most preferably from 2 to 5. Examples of such suitable secondary anionic stabilizing agents include, but are not limited to, phosphoric acid ($pK_a$ 2.2), organic acids, such as acetic acid ($pK_a$ 4.8), benzoic acid ($pK_a$ 4.2), chloroacetic acid ($pK_a$ 2.9), cyanoacetic acid, and mixtures thereof. Preferably these secondary anionic stabilizing agents are organic acids, such as acetic acid or benzoic acid. In embodiments, the amount of acetic acid and/or benzoic acid is about 25–500 ppm. The concentration of acetic acid is typically 50–400 ppm, preferably 75–300 ppm, and more preferably 100–200 ppm. When using a stronger acid such as phosphoric acid, a concentration of 20–100 ppm, preferably 30–80 ppm, and more preferably 40–60 ppm may be utilized.

Combinations of at least one vapor phase stabilizer and at least one liquid phase anionic stabilizer are preferred. For example, combinations of sulfur dioxide and sulfuric acid, sulfur dioxide and perchloric acid, sulfur dioxide and chlorosulfonic acid, boron trifluoride and sulfuric acid, boron trifluoride and perchloric acid, boron trifluoride and chlorosulfonic acid, boron trifluoride and methanesulfonic acid, hydrogen fluoride and sulfuric acid, hydrogen fluoride and perchloric acid, hydrogen fluoride and chlorosulfonic acid, and hydrogen fluoride and methanesulfonic acid can be used. A combination of boron trifluoride, sulfur dioxide, and sulfuric acid can also be used, among other combinations. The two types of anionic stabilizers are chosen in conjunction such that the stabilizers are compatible with the chosen adhesive composition and each other stabilizer, as well as with the packaging material and the equipment used to make and package the composition. In other words, the combination of vapor phase stabilizer(s), liquid phase stabilizer(s), and monomer should be such that a stabilized, substantially unpolymerized adhesive composition is present after packaging.

Medical compositions of the present invention may also include at least one biocompatible agent effective to reduce active formaldehyde concentration levels produced during in vivo biodegradation of the polymer (also referred to herein as "formaldehyde concentration reducing agents"). Preferably, this component is a formaldehyde scavenger compound. Examples of formaldehyde scavenger compounds useful in this invention include sulfites; bisulfites; mixtures of sulfites and bisulfites; ammonium sulfite salts; amines; amides; imides; nitriles; carbamates; alcohols; mercaptans; proteins; mixtures of amines, amides, and proteins; active methylene compounds such as cyclic ketones and compounds having a b-dicarbonyl group; and heterocyclic ring compounds free of a carbonyl group and containing an NH group, with the ring made up of nitrogen or carbon atoms, the ring being unsaturated or, when fused to a phenyl group, being unsaturated or saturated, and the NH group being bonded to a carbon or a nitrogen atom, which atom is directly bonded by a double bond to another carbon or nitrogen atom.

Bisulfites and sulfites useful as the formaldehyde scavenger compound in this invention include alkali metal salts such as lithium, sodium, and potassium salts, and ammonium salts, for example, sodium bisulfite, potassium bisulfite, lithium bisulfite, ammonium bisulfite, sodium sulfite, potassium sulfite, lithium sulfite, ammonium sulfite, and the like.

Examples of amines useful in this invention include the aliphatic and aromatic amines such as, for example, aniline, benzidine, aminopyrimidine, toluene-diamine, triethylenediamine, diphenylamine, diaminodiphenylamine, hydrazines, and hydrazide.

Suitable proteins include collagen, gelatin, casein, soybean protein, vegetable protein, keratin, and glue. The preferred protein for use in this invention is casein.

Suitable amides for use in this invention include urea, cyanamide, acrylamide, benzamide, and acetamide. Urea is a preferred amide.

Suitable alcohols include phenols, 1,4-butanediol, d-sorbitol, and polyvinyl alcohol.

Examples of suitable compounds having a b-dicarbonyl group include malonic acid, acetylacetone, ethylacetone, acetate, malonamide, diethylmalonate, or another malonic ester.

Preferred cyclic ketones for use in this invention include cyclohexanone or cyclopentanone.

Examples of suitable heterocyclic compounds for use as the formaldehyde scavenger in this invention are disclosed, for example, in U.S. Pat. No. 4,127,382 to Perry, which is hereby incorporated in its entirety by reference. Such heterocyclic compounds include, for example, benzimidazole, 5-methyl benzimidazole, 2-methylbenzimidazole, indole, pyrrole, 1,2,4-triazole, indoline, benzotriazole, indoline, and the like.

A formaldehyde concentration reducing or scavenging agent can be added in an effective amount to the cyanoacrylate. The "effective amount" is that amount sufficient to reduce the amount of formaldehyde generated during subsequent in vivo biodegradation of the polymerized cyanoacrylate. This amount will depend on the type of active formaldehyde concentration reducing agent, and can be readily determined without undue experimentation by those skilled in the art. A preferred formaldehyde scavenger is sodium bisulfite.

The formaldehyde concentration reducing agent may be used in this invention in either free form or in microencapsulated form. When microencapsulated, the formaldehyde concentration reducing agent is released from the microcapsule continuously over a period of time during the in vivo biodegradation of the cyanoacrylate polymer.

For purposes of this invention, the microencapsulated form of the formaldehyde concentration reducing agent is preferred because this embodiment prevents or substantially reduces polymerization of the cyanoacrylate monomer by the formaldehyde concentration reducing agent, which increases shelf-life and facilitates handling of the monomer composition during use.

Microencapsulation of the formaldehyde scavenger can be achieved by many known microencapsulation techniques. For example, microencapsulation can be carried out by dissolving a coating polymer in a volatile solvent, e.g., methylene chloride, to a polymer concentration of about 6% by weight; adding a formaldehyde scavenger compound in particulate form to the coating polymer/solvent solution under agitation to yield a scavenger concentration of 18% by weight; slowly adding a surfactant-containing mineral oil solution to the polymer solution under rapid agitation; allowing the volatile solvent to evaporate under agitation; removing the agitator; separating the solids from the mineral oil; and washing and drying the microparticles. The size of the microparticles will range from about 0.001 to about 1000 microns.

The coating polymer for microencapsulating the formaldehyde concentration reducing agent should be polymers which undergo in vivo bioerosion, preferably at rates similar to or greater than the cyanoacrylate polymer formed by the monomer, and should have low inherent moisture content. Such bioerosion can occur as a result of the physical or chemical breakdown of the encapsulating material, for example, by the encapsulating material passing from solid to solute in the presence of body fluids, or by biodegradation of the encapsulating material by agents present in the body.

Examples of coating materials which can be used to microencapsulate the formaldehyde concentration reducing agent include polyesters, such as polyglycolic acid, polylactic acid, poly-1,4-dioxa-2-one, polyoxaltes, polycarbonates, copolymers of polyglycolic acid and polylactic acid, polycaprolactone, poly-b-hydroxybutyrate, copolymers of epsilon-caprolactone and delta-valerolactone, copolymers of epsilon-caprolactone and DL-dilactide, and polyester hydrogels; polyvinylpyrrolidone; polyamides; gelatin; albumin; proteins; collagen; poly(orthoesters); poly (anhydrides); poly(alkyl-2-cyanoacrylates); poly (dihydropyrans); poly(acetals); poly(phosphazenes); poly (urethanes); poly(dioxinones); cellulose; and starches.

Examples of surfactants which can be added to the mineral oil include those commercially available under the designations Triton X-100™ (Rohm and Haas) (octoxynol), Tween 20™ (ICI Americas) (polysorbate), and Tween 80™ (ICI Americas) (polysorbate).

To improve the cohesive strength of adhesives formed from the compositions of this invention, difunctional monomeric cross-linking agents may be added to the monomer compositions of this invention. Such crosslinking agents are known. U.S. Pat. No. 3,940,362 to Overhults, which is hereby incorporated in its entirety by reference, discloses such cross-linking agents. Examples of suitable crosslinking agents include alkyl bis(2-cyanoacrylates), triallyl isocyanurates, alkylene diacrylates, alkylene dimethacrylates, trimethylol propane triacrylate, and alkyl bis(2-cyanoacrylates). A catalytic amount of an amine activated free radical initiator or rate modifier may be added to initiate polymerization or to modify the rate of polymerization of the cyanoacrylate monomer/crosslinking agent blend.

In embodiments of the present invention, the applicator may contain a polymerization initiator or accelerator and/or cross-linking agent for initiating polymerization and/or cross-linking of the polymerizable monomer material.

The initiators or accelerators (hereinafter jointly referred to as initiators) may be applied to a surface portion or to the entire surface of the applicator tip, including the interior and the exterior of the tip. Alternatively, the initiator may be coated only on an internal surface of the applicator tip. Preferably, only a portion of the interior of the applicator tip is coated with the initiator. Placing the initiator on or in the applicator tip is particularly useful in embodiments where the applicator body is reused, but different applicator tips are used for the subsequent adhesive applications.

In other embodiments, the initiator can be coated on an interior surface of the applicator body or and/on an exterior surface of an ampoule or other container disposed within the applicator body, can be placed in the applicator body in the form of a second frangible vial or ampoule and/or can be otherwise contained within the applicator body, so long as a non-contacting relationship between the polymerizable monomer composition and the initiator is maintained until use of the adhesive.

The initiator may be in the form of a solid, such as a powder or a solid film, or in the form of a liquid, such as a viscous or paste-like material. The initiator may also include a variety of additives, such as surfactants or emulsifiers. Preferably, the initiator is soluble in the polymerizable and/or cross-linkable material, and/or comprises or is accompanied by at least one surfactant which, in embodiments, helps the initiator co-elute with the polymerizable and/or cross-linkable material. In embodiments, the surfactant may help solubilize the initiator in the polymerizable and/or cross-linkable material.

Particular initiators for particular systems may be readily selected by one of ordinary skill in the art without undue experimentation. Suitable initiators include, but are not limited to, detergent compositions; surfactants: e.g., non-ionic surfactants such as polysorbate 20 (e.g., Tween 20™ from ICI Americas), polysorbate 80 (e.g., Tween 80™ from ICI Americas) and poloxamers, cationic surfactants such as tetrabutylammonium bromide, anionic surfactants such as sodium tetradecyl sulfate, and amphoteric or zwitterionic surfactants such as dodecyldimethyl(3-sulfopropyl) ammonium hydroxide, inner salt; amines, imines and amides, such as imidazole, tryptamine, urea, arginine and povidine; phosphines, phosphites and phosphonium salts, such as triphenylphosphine and triethyl phosphite; alcohols such as ethylene glycol, methyl gallate, ascorbic acid, tannins and tannic acid; inorganic bases and salts, such as sodium bisulfite, magnesium hydroxide, calcium sulfate and sodium silicate; sulfur compounds such as thiourea and polysulfides; polymeric cyclic ethers such as monensin, nonactin, crown ethers, calixarenes and polymeric epoxides; cyclic and acyclic carbonates, such as diethyl carbonate; phase transfer catalysts such as Aliquat 336; organometallics such as cobalt naphthenate and manganese acetylacetonate; and radical initiators and radicals, such as di-t-butyl peroxide and azobisisobutyronitrile. The polymerizable and/or cross-linkable material may also contain an initiator that is inactive until activated by a catalyst or accelerator (included within the scope of the term "initiator" as used herein) also contained in the applicator, such as in the applicator tip. For example, monomer containing benzoyl peroxide may be used as a polymerizable material in association with a tip containing an amine accelerator, or monomer containing methyl ethyl ketone peroxide may be used as a polymerizable material in association with a tip containing cobalt naphthenate. Initiators activated by stimulation such as heat and/or light (e.g., ultraviolet or visible light) are also suitable if the tip and/or applicator is appropriately subjected to such stimulation.

When the initiator is contained in or on an applicator tip, the initiator may be applied to the surface of the applicator tip or may be impregnated or incorporated into the matrix or internal portions of the applicator tip. For example, the initiator may be applied to the applicator tip by spraying, dipping, or brushing the applicator tip with a liquid medium containing the initiator. The liquid medium may include non-aqueous solvents, such as ether, acetone, methanol, ethanol, pentane or mixtures thereof; or may include aqueous solutions. Preferably, the liquid medium is a low boiling point solvent. Additionally, the initiator on the applicator tip may be present in a variety of concentrations in the medium ranging from 0 to 50%, preferably from 0.001 to 25%, and most preferably from 0.01 to 10% by wt. Selection of the amount will, of course, depend on the desired monomer and process conditions, and amounts outside these ranges may be acceptable.

The initiator may be applied to the applicator tip in the form of a preformed film of initiator. The initiator may be applied as a solid by vapor deposition such as by sputtering. Additionally, the initiator may be incorporated into the applicator tip, for example, during the fabrication of the tip. This can be accomplished by mixing the initiator with the applicator tip material prior to molding the applicator tip material into the desired form.

Any suitable structure or methodology may be used to incorporate the initiator or rate modifier into the applicator, so long as the initiator or rate modifier becomes accessible to the polymerizable monomer composition during application of the composition to a substrate. For example, various designs of applicators and methods for incorporating the initiator or rate modifier into the applicator are disclosed in U.S. Pat. No. 5,928,611 and U.S. patent applications Ser. No. 09/069,979, filed Apr. 30, 1998, and Ser. No. 09/069, 875, filed Apr. 30, 1998, the entire disclosures of which are incorporated herein by reference.

The compositions of this invention may further contain fibrous reinforcement and colorants such as dyes, pigments, and pigment dyes. Examples of suitable fibrous reinforcement include PGA microfibrils, collagen microfibrils, cellulosic microfibrils, and olefinic microfibrils. Examples of suitable colorants include 1-hydroxy-4-[4-methylphenyl-amino]-9,10 anthracenedione (D+C violet No. 2); disodium salt of 6-hydroxy-5-[(4-sulfophenyl)axo]-2-naphthalene-sulfonic acid (FD+C Yellow No. 6); 9-(o-carboxyphenoyl)-6-hydroxy-2,4,5,7-tetraiodo-3H-xanthen-3-one, disodium salt, monohydrate (FD+C Red No. 3); 2-(1,3-dihydro-3-oxo-5-sulfo-2H-indol-2-ylidene)-2,3-dihydro-3-oxo-1H-indole-5-sulfonic acid disodium salt (FD+C Blue No. 2); and [phthalocyaninato (2-)] copper.

Other compositions contemplated by the present invention are exemplified by U.S. Pat. Nos. 5,624,669; 5,582,834; 5,575,997; 5,514,371; 5,514,372; and 5,259,835; and U.S. patent application Ser. No. 08/714,288, the disclosures of all of which are hereby incorporated in their entirety by reference.

Examples 1–11 and Comparative Examples 1–7

Various 2-octyl cyanoacrylate monomer compositions are prepared by adding a selected amount of an antimicrobial agent to 2 mL of 2-octyl cyanoacrylate monomer. The mixture is then sealed in a glass vial and stirred. Specific antimicrobial agents and the respective amounts added are identified in the following Table I.

The characteristics of the compositions are recorded at about one minute after preparation and at twenty-four or more hours after preparation. The results of the observations are also reported in Table I. All solutions that are indicated as "Clear" are solutions in which the respective antimicrobial agent is soluble in the monomer.

Examples 12–21 and Comparative Example 8

Adhesive compositions are prepared by adding the pharmaceutically regulated amount of a specific antimicrobial

TABLE I

| Example | Compound | Amount Added | Notes @ ~ 1 min | Notes @ 24+ Hours |
|---|---|---|---|---|
| 1 | Benzoic Acid | ~30 mg | Solid in Solution | Clear |
| 2 | Butylparaben | ~30 mg | Clear | Clear |
| 3 | Chlorobutanol | 100 uL | Clear | Clear |
| 4 | Chlorocresol | ~30 mg | Clear | Clear |
| 5 | Cresol | 100 uL | Clear | Clear |
| 6 | Dehydroacetic Acid | ~30 mg | Clear | Clear |
| 7 | Ethylparaben | 67 mg | Clear | Clear |
| 8 | Methylparaben | ~30 mg | Clear | Clear |
| 9 | Phenol | ~30 mg | Clear | Clear |
| Comp 1 | Phenylmercuric Acetate | ~30 mg | Polymerized | Polymerized |
| Comp 2 | Phenylmercuric Nitrate | ~30 mg | Yellow Suspension | Falls out of Solution |
| Comp 3 | Potassium Benzoate | ~30 mg | Polymerized | Polymerized |
| 10 | Propylparaben | 100 mg | Clear | Clear |
| Comp 4 | Sodium Benzoate | ~30 mg | Polymerized | Polymerized |
| Comp 5 | Sodium Propionate | ~30 mg | Polymerized | Polymerized |
| Comp 6 | Sorbic Acid | ~30 mg | Suspension | Suspension |
| Comp 7 | Thimerosal (sodium salt) | ~30 mg | Polymerized | Polymerized |
| 11 | Thymol | ~30 mg | Clear | Clear |

"Suspension" in Comparative Example 6 indicates that insoluble material is present, but is not completely settled to the bottom of the container.

The results show that not all antimicrobial agents are soluble and/or stable in the monomer. In particular, although each of Examples 1–11 and Comparative Examples 1–7 include the antimicrobial agent in generally comparable amounts, the monomer compositions in Comparative Examples 1–7 demonstrate either insolubility of the antimicrobial agent in the monomer, or premature polymerization of the monomer after being mixed with the antimicrobial agent.

agent to 2-octyl cyanoacrylate. A control composition (Comparative Example 8) is also prepared using a 2-octyl cyanoacrylate but not including any additional antimicrobial agent. All of the solutions are subjected to a simulated shelf-life of 0 and 2 years. After this procedure, the viscosity of each of the solutions is measured. This experiment is then repeated adding a sterilization cycle first and then subjecting the solutions to the same simulated shelf-life conditions. Again, after the procedure, the viscosity of each of the solutions is measured. The measured viscosity values are set forth in Table II, below, where each data point is an average of three readings.

TABLE II

| | | Viscosity, cP | | | |
|---|---|---|---|---|---|
| Example | Antimicrobial Agent | Zero Years Without Sterilization | Two Years Simulated Shelf-Life Without Sterilization | Zero Years Post Sterilization | Two Years Simulated Shelf-Life Post Sterilization |
| Comp. 8 | None | 6.1 +/- 0.1 | 21.0 +/- 10.0 | 6.6 +/- 0.1 | 20.4 +/- 1.8 |
| 12 | Benzoic Acid | 6.1 +/- 0.1 | 60.0 +/- 6.5 | 7.2 +/- 0.1 | 38.3 +/- 2.9 |
| 13 | 4-Chloro-1-Butanol (85%) | 6.1 +/- 0.0 | 18.0 +/- 1.0 | 7.1 +/- 0.1 | Thick |
| 14 | 2-Chloro-5-Methyl Phenol | 6.2 +/- 0.1 | 30.0 +/- 4.6 | 7.0 +/- 0.1 | 309.1 +/- 244 |
| 15 | 2-Methoxy-4-MethylPhenol | 6.3 +/- 0.1 | 46.0 +/- 11.2 | 9.6 +/- 1.1 | 216.4 +/- 27.6 |
| 16 | Dehydroacetic Acid | 6.2 +/- 0.1 | 44.0 +/- 5.1 | 9.0 +/- 0.1 | 72.6 +/- 39.8 |
| 17 | Ethyl-4-HydroxyBenzoate | 6.3 +/- 0.0 | 46.0 +/- 6.7 | 8.0 +/- 0.3 | 99.0 +/- 12.0 |
| 18 | Methyl-4-HydroxyBenzoate | 6.5 +/- 0.1 | 50.0 +/- 2.1 | 9.7 +/- 0.6 | 210.0 +/- 88.2 |
| 19 | Phenol | 6.4 +/- 0.1 | 48.0 +/- 4.9 | 8.9 +/- 0.1 | 85.0 +/- 37.7 |
| 20 | Propyl-4-HydroxyBenzoate | 6.1 +/- 0.1 | 46.0 +/- 4.9 | 8.6 +/- 0.3 | 111.0 +/- 7.2 |
| 21 | Thymol | 6.2 +/- 0.1 | 49.0 +/- 3.2 | 8.5 +/- 1.1 | 209.0 +/- 7.6* |

*One sample was too thick to read.

The results in Table II demonstrate that incorporation of the antimicrobial agent does not adversely affect the stability of the monomer composition. Although the viscosities of the compositions generally increase after the sterilization procedures, stability of most of the compositions is not lost. However, as noted in Table II, several samples in Examples 13 and 21 become too thick to measure the viscosity, likely due to premature polymerization of the monomer. The remaining compositions, although having a viscosity generally higher than the viscosity of the control (Comparative Example 8), still exhibit commercially acceptable stability following the sterilization procedure.

Examples 22–31 and Comparative Example 9

Various adhesive compositions are prepared by adding the pharmaceutically regulated amount of specific antimicrobial agents to 2-octyl cyanoacrylate. A control composition (Comparative Example 9) is also prepared using a 2-octyl cyanoacrylate but not including any antimicrobial agent. All of the solutions are subjected to a simulated shelf-life of two years. After this procedure, the viscosity of each of the solutions is measured. This experiment is then repeated adding a different sterilization procedure first and then subjecting the solutions to the same simulated shelf-life conditions for 0, 1 and 2 years. Again, after the procedure, the viscosity of each of the solutions is measured. The measured viscosity values are set forth in Table III, below. Each data point is an average of four readings.

Furthermore, a comparison of the results in Tables II and III demonstrate that some of the antimicrobial agents are compatible with some forms of sterilization, but are incompatible with other forms of sterilization. For example, comparison of Examples 16 and 26 shows that the antimicrobial agent dehydroacetic acid is compatible with one form of sterilization, but is incompatible with another form of sterilization. Likewise, comparison of Examples 21 and 31 shows that the antimicrobial agent thymol is more compatible with one form of sterilization than it is with another form of sterilization.

While the invention has been described with reference to preferred embodiments, the invention is not limited to the specific examples given, and other embodiments and modifications can be made by those skilled in the art without departing from the spirit and scope of the invention.

What is claimed is:

1. A monomeric adhesive composition comprising a polymerizable alkyl cyanoacrylate monomer and an antimicrobial preservative agent, wherein said agent is soluble in said monomer at room temperature and substantially all of said monomer remains stable for at least five minutes after forming the composition, wherein said agent is selected from the group consisting of parabens, cresols, pyrocatechol, resorcinol, 4-n-hexyl resorcinol, 3a,4,7,7a-tetrahydro-2-((trichloromethyl)thio)-1H-isoindole-1,3(2H)-dione, benzyl alcohol, chlorobutanol, dehydroacetic acid, methylparaben sodium, o-phenylphenol, phenylethyl

TABLE III

| | | Viscosity, cP | | | | |
| --- | --- | --- | --- | --- | --- | --- |
| Example | Antimicrobial Agent | Zero Days Without Sterilization | Two Years Simulated Shelf-Life Without Sterilization | Zero Years Post Sterilization | One Year Simulated Shelf-Life Post Sterilization | Two Years Simulated Shelf-Life Post Sterilization |
| Comparative 9 | None | 6.2 +/− 0.0 | 10.3 +/− 1.1 | 11.6 +/− 0.8 | Thick | Thick |
| 22 | Benzoic Acid | 6.3 +/− 0.3 | 26.7 +/− 2.3 | 10.7 +/− 0.3 | Thick | Thick |
| 23 | 4-Chloro-1-Butanol (85%) | 6.0 +/− 0.2 | 11.1 +/− 0.2 | 9.7 +/− 0.6 | Solid | Solid |
| 24 | 2-Chloro-5-Methyl Phenol | 6.4 +/− 0.3 | 15.7 +/− 5.4 | 10.9 +/− 0.4 | 72.9 +/− 10.1 | Solid |
| 25 | 2-Methoxy-4-Methyl Phenol | 6.2 +/− 0.3 | 19.3 +/− 1.6 | 9.8 +/− 0.5 | 34.9 +/− 5.7 | Solid |
| 26 | Dehydroacetic Acid | 6.6 +/− 0.4 | 46.8 +/− 10.2 | Solid | Solid | Solid |
| 27 | Ethyl-4-Hydroxy Benzoate | 6.2 +/− 0.1 | 22.0 +/− 2.4 | 9.7 +/− 0.4 | 141.7 +/− 35.8 | Solid |
| 28 | Methyl-4-Hydroxy Benzoate | 6.2 +/− 0.3 | 13.9 +/− 1.4 | 10.7 +/− 0.3 | 39.0 +/− 13.2 | 392.4 +/− 44.7 |
| 29 | Phenol | 6.2 +/− 0.2 | 16.0 +/− 0.5 | 10.1 +/− 0.9 | 47.8 +/− 23.5 | Thick |
| 30 | Propyl-4-HydroxyBenzoate | 6.1 +/− 0.2 | 12.7 +/− 1.9 | 10.4 +/− 0.7 | 23.1 +/− 0.8 | 136.8 +/− 5.5 |
| 31 | Thymol | 6.2 +/− 0.1 | 18.2 +/− 1.8 | 10.3 +/− 0.2 | 33.8 +/− 3.8 | Thick |

The results in Table III demonstrate that incorporation of the antimicrobial agent does not adversely affect the stability of the monomer composition. Although the viscosities of the compositions generally increase during the procedure that is used to simulate longer periods of shelf-life, and after the sterilization procedure, stability of most of the compositions is not lost. However, as noted in Table III, several samples in Example 26 become solid after the sterilization procedure, and several samples in Comparative Example 9 become too thick to measure the viscosity following the sterilization, likely due to premature polymerization of the monomer. Similarly, many of the samples in the Examples turn to solid during the simulated shelf-life procedure, indicating that the compositions tend to prematurely polymerize over time, i.e., indicating that these samples have a shorter shelf-life than the other samples. The remaining compositions, although having a viscosity generally higher than the viscosity of the control (Comparative Example 9), still exhibit commercially acceptable stability following the sterilization procedure.

alcohol, phenylmercuric acetate, phenylmercuric borate, phenylmercuric nitrate, potassium benzoate, potassium sorbate, propylparaben sodium, sodium benzoate, sodium dehydroacetate, sodium propionate, sorbic acid, thimerosal, 4-chloro-1-butanol, methyl-4-hydroxy benzoate, elemental metals and metal compounds, and a non-polymer stabilized material that is soluble or insoluble in the monomer.

2. The composition of claim 1, wherein said composition remains stable for at least one hour after forming the composition.

3. The composition of claim 1, wherein said composition remains stable for at least twenty-four hours after forming the composition.

4. The composition of claim 1, wherein said composition remains stable for at least eighteen months after forming the composition.

5. The composition of claim 1, wherein said composition remains stable for at least twenty-four months after forming the composition.

6. The composition of claim 1, wherein a concentration of said agent is substantially uniform throughout said composition.

7. The composition of claim 1, wherein said monomer is at least one member selected from the group consisting of n-butyl cyanoacrylate, 2-octyl cyanoacrylate, and ethyl cyanoacrylate.

8. The composition of claim 1, wherein said agent is selected from the group consisting of parabens and cresols.

9. The composition of claim 1, wherein said agent is selected from the group consisting of alkyl parabens having an alkyl group of from 1–4 carbon atoms.

10. The composition of claim 1, wherein said agent is methylparaben.

11. The composition of claim 1, wherein said agent is selected from the group consisting of pyrocatechol, resorcinol, 4-n-hexyl resorcinol, 3a,4,7,7a-tetrahydro-2-((trichloromethyl)thio)-1H-isoindole-1,3(2H)-dione, benzyl alcohol, butylparaben, chlorobutanol, chlorocresol, cresol, dehydroacetic acid, ethylparaben, methylparaben, methylparaben sodium, o-phenylphenol, phenylethyl alcohol, phenylmercuric acetate, phenylmercuric borate, phenylmercuric nitrate, potassium benzoate, potassium sorbate, propylparaben, propylparaben sodium, sodium benzoate, sodium dehydroacetate, sodium propionate, sorbic acid, and thimerosal.

12. A method of making a sterile, antimicrobial adhesive composition comprising:

placing a mixture of a polymerizable alkyl cyanoacrylate monomer and an antimicrobial preservative agent in a container, sealing said container, and sterilizing the mixture in the container, wherein said mixture remains stable for at least five minutes after forming the mixture, and wherein said agent is selected from the group consisting of parabens, cresols, pyrocatechol, resorcinol, 4-n-hexyl resorcinol, 3a,4,7,7a-tetrahydro-2-((trichloromethyl)thio)-1H-isoindole-1,3(2H)-dione, benzyl alcohol, chlorobutanol, dehydroacetic acid, methylparaben sodium, o-phenylphenol, phenylethyl alcohol, phenylmercuric acetate, phenylmercuric borate, phenylmercuric nitrate, potassium benzoate, potassium sorbate, propylparaben sodium, sodium benzoate, sodium dehydroacetate, sodium propionate, sorbic acid, thimerosal, 4-chloro-1-butanol, methyl-4-hydroxy benzoate, elemental metals and metal compounds, and a non-polymer stabilized material that is soluble or insoluble in the monomer.

13. The composition of claim 1, wherein said agent is 4-chloro-1-butanol.

14. The method of claim 12, wherein said agent is selected from the group consisting of methylparaben, ethylparaben, propylparaben, butylparaben, and mixtures thereof.

15. The method of claim 12, wherein said mixture further comprises at least one stabilizer.

16. The composition of claim 1, wherein said agent is methyl-4-hydroxy benzoate.

17. The composition of claim 1, wherein said agent is selected from the group consisting of elemental metals and metal compounds.

18. The composition of claim 1, wherein said agent is an elemental metal selected from the group consisting of silver and copper.

19. The composition of claim 1, wherein said agent is a metal compound selected from the group consisting of mercurial compounds, copper chloride, copper sulfate, copper peptides, zinc chloride, zinc sulfate, silver nitrate, silver iodide, silver acetate, silver benzoate, silver carbonate, silver chloride, silver citrate, silver oxide, silver sulfate, and tincture of iodine.

20. The composition of claim 1, wherein said agent is a mercurial compound selected from the group consisting of phenolmercuric chloride, phenolmercuric acetate, acetomeroctol, nitromersol, thimerosal, mercurochrome, mercuric chloride, and mercuric iodide.

21. The composition of claim 1, wherein said agent is provided by a non-polymer stabilized material that is soluble or insoluble in the monomer.

22. The composition of claim 21, wherein said agent comprises ions released by said material.

23. The composition of claim 21, wherein said material is insoluble in the monomer.

24. The composition of claim 21, wherein said material is in a form selected from the group consisting of a hollow sphere, a solid ball, a cube, and a flat sheet.

25. The composition of claim 1, wherein said agent is a zinc compound.

26. The composition of claim 1, wherein said agent is selected from the group consisting of methylparaben, ethylparaben, propylparaben, butylparaben, and mixtures thereof.

27. The composition of claim 25, wherein said zinc compound is selected from the group consisting of zinc salts of cyanoacrylic acid, zinc salts of cyanoacetic acid, zinc salts of dicyanoglutaric acid, zinc salts of rosin, zinc oxide, zinc salts of polycyanoacrylic acid, zinc salts of polyacrylic acid, zinc bacitracin, zinc salicylate, zinc stearate, zinc citrate, zinc lactate, and mixtures thereof.

28. The composition of claim 1, wherein said composition has a viscosity of about 1–5000 centipoise at 25° C.

29. The composition of claim 1, wherein said composition has a viscosity of about 3–600 centipoise at 25° C.

30. The composition of claim 1, wherein said composition has a viscosity of about 4–50 or 100–250 centipoise at 25° C.

31. The composition of claim 1, wherein said composition is a gel.

32. The composition of claim 1, wherein said composition further comprises a plasticizing agent.

33. The composition of claim 1, wherein said composition is sterile.

34. The composition of claim 1, wherein said composition is packaged in a single-use container.

35. The composition of claim 1, wherein said composition is packaged in a multi-use container.

36. A method of making a monomeric adhesive composition, comprising dissolving an antimicrobial preservative agent in a polymerizable alkyl cyanoacrylate monomer, wherein said agent is soluble in the monomer at room temperature and said composition remains stable for at least five minutes after forming the composition, wherein said agent is selected from the group consisting of parabens, cresols, pyrocatechol, resorcinol, 4-n-hexyl resorcinol, 3a,4,7,7a-tetrahydro-2-((trichloromethyl)thio)-1H-isoindole-1,3(2H)-dione, benzyl alcohol, chlorobutanol, dehydroacetic acid, methylparaben sodium, o-phenylphenol, phenylethyl alcohol, phenylmercuric acetate, phenylmercuric borate, phenylmercuric nitrate, potassium benzoate, potassium sorbate, propylparaben sodium, sodium benzoate, sodium dehydroacetate, sodium propionate, sorbic acid, thimerosal, 4-chloro-1-butanol, methyl-4- hydroxy benzoate, elemental metals and metal compounds, and a non-polymer stabilized material that is soluble or insoluble in the monomer.

37. The method of claim 36, wherein said composition remains stable for at least one hour after forming the composition.

38. The method of claim 36, wherein said composition remains stable for at least twenty-four hours after forming the composition.

39. The method of claim 36, wherein said composition remains stable for at least eighteen months after forming the composition.

40. The method of claim 36, wherein said composition remains stable for at least twenty-four months after forming the composition.

41. The method of claim 36, wherein a concentration of said agent is substantially uniform throughout said composition.

42. The method of claim 36, wherein said agent is provided by a non-polymer stabilized material that is soluble or insoluble in the monomer.

43. The method of claim 42, wherein said agent comprises ions released by said material.

44. The method of claim 42, wherein said material is insoluble in the monomer.

45. The method of claim 36, further comprising sterilizing said mixture.

46. The method of claim 36, wherein said agent is selected from the group consisting of methylparaben, ethylparaben, propylparaben, butylparaben, and mixtures thereof.

47. The method of claim 12, wherein said mixture remains stable for at least one hour after forming the composition.

48. The method of claim 12, wherein said mixture remains stable for at least twenty-four hours after forming the composition.

49. The method of claim 12, wherein said composition remains stable for at least eighteen months after forming the composition.

50. The method of claim 12, wherein said composition remains stable for at least twenty-four months after forming the composition.

51. The method of claim 12, wherein said agent is soluble in said monomer at room temperature and said mixture is a solution.

52. The method of claim 51, wherein a concentration of said agent is substantially uniform throughout said solution.

53. The method of claim 12, wherein said sterilizing is performed by dry heat, moist heat, gamma irradiation, electron beam irradiation, microwave irradiation, or retort canning.

54. The method of claim 12, wherein said sterilizing is performed by dry heat.

55. The method of claim 12, wherein said sterilizing is performed by gamma irradiation.

56. The method of claim 12, wherein said sterilizing is performed by electron beam irradiation.

57. The method of claim 12, wherein said sterilizing is performed by retort canning.

58. The method of claim 12, wherein said container is made from at least one material selected from the group consisting of glass, plastic, and metal.

59. The method of claim 12, wherein said container is made from plastic.

60. The method of claim 12, wherein said container is made from glass.

* * * * *